United States Patent
Olsen et al.

[11] Patent Number: 6,099,519
[45] Date of Patent: Aug. 8, 2000

[54] CATHETER SLEEVE CONNECTING ASSEMBLY

[75] Inventors: Harry O. Olsen, Warwick, R.I.; David L. Brodsky, West Palm Beach, Fla.

[73] Assignee: Tyco Healthcare Group LP

[21] Appl. No.: 08/651,203

[22] Filed: May 17, 1996

Related U.S. Application Data

[63] Continuation of application No. 08/282,727, Jul. 29, 1994, abandoned.

[51] Int. Cl.[7] .................................................. A61M 25/16
[52] U.S. Cl. ........................ 604/534; 604/171; 604/533
[58] Field of Search ................................. 604/171, 280, 604/283, 905; 128/DIG. 26

[56] References Cited

U.S. PATENT DOCUMENTS

| | | | |
|---|---|---|---|
| 4,006,744 | 2/1977 | Steer ........................................ | 604/283 |
| 4,054,135 | 10/1977 | Berman . | |
| 4,249,529 | 2/1981 | Nestor et al. . | |
| 4,402,691 | 9/1983 | Rosenthal et al. ....................... | 604/411 |
| 4,405,312 | 9/1983 | Gross et al. ............................... | 604/29 |
| 4,473,369 | 9/1984 | Lueders et al. .......................... | 604/244 |
| 4,557,261 | 12/1985 | Rügheimer . | |
| 4,569,344 | 2/1986 | Palmer . | |
| 4,631,056 | 12/1986 | Dye .......................................... | 604/111 |
| 4,675,007 | 6/1987 | Terry ........................................ | 604/283 |
| 4,723,948 | 2/1988 | Clark et al. .............................. | 604/283 |
| 4,772,268 | 9/1988 | Bates . | |
| 4,829,145 | 5/1989 | Mitchell et al. . | |
| 5,037,405 | 8/1991 | Crosby ..................................... | 604/283 |
| 5,069,206 | 12/1991 | Crosbie . | |
| 5,215,531 | 6/1993 | Maxson et al. . | |
| 5,226,892 | 7/1993 | Boswell . | |
| 5,267,970 | 12/1993 | Chin et al. . | |
| 5,355,876 | 10/1994 | Brodsky et al. . | |

FOREIGN PATENT DOCUMENTS

| | | | |
|---|---|---|---|
| 0183396 | 6/1986 | European Pat. Off. ................ | 604/283 |
| 0 589 577 A1 | 3/1994 | European Pat. Off. . | |
| 0 603 609 A2 | 6/1994 | European Pat. Off. . | |

*Primary Examiner*—Corrine McDermott

[57] ABSTRACT

An apparatus for connecting a flexible sleeve to a fitting. At one end of the fitting is a tubular extension configured and dimensioned for insertion into one end of the flexible sleeve. A split collar having semi-circular segments is placed into an operative position tightly surrounding the sleeve end and the tubular extension inserted therein. The segments of the collar are coactively interengaged in an axially and rotationally fixed relationship with respect to the tubular extension.

18 Claims, 2 Drawing Sheets

CATHETER SLEEVE CONNECTING ASSEMBLY

This is a continuation of application Ser. No. 08/282,727 filed Jul. 29, 1994 now abandoned.

BACKGROUND OF THE INVENTION

1. Field of the Invention

This invention relates to medical devices of the type used to ventilate and aspirate the respiratory systems of patients.

2. Background of the Invention

In a preferred medical device of the type referred to above, as described for example in U.S. patent application Ser. No. 07/878,968 filed on May 6, 1992, the description of which is herein incorporated by reference, an aspirating catheter is enclosed within a flexible sleeve having tubular fittings at its opposite ends. The fittings are adapted to detachably secure the opposite ends of the sleeve respectively to a vacuum control valve and to a patient module connected to a tracheostomy device installed in the trachea of a patient. The sleeve ends are threaded through mounting collars which are then assembled in a linear interference fit on the fittings, thereby sandwiching the sleeve material therebetween. The mounting collars and tubular fittings have circular ribs which coact to resist axial disengagement.

This type of arrangement has several drawbacks, including a tendency of the mounting collars to rotate with respect to the tubular fittings on which they are mounted, and poor holding ability of the coacting circular ribs and grooves. These drawbacks can be minimized to some extent by solvent bonding or ultrasonic welding the mounting collars to the fittings, but these additional procedures contribute unfavorably to the overall cost of the resulting product.

A further disadvantage of the aforesaid arrangements is the need to thread each end of the sleeve through a mounting collar before axially inserting the sleeve ends and collars on the tubular fittings. This extra threading step is both time consuming and somewhat difficult to perform quickly, thus adding unnecessarily to assembly costs.

The objective of the present invention is to obviate the disadvantages and drawbacks of the prior art by providing an improved means for connecting the sleeve ends to the tubular fittings used to detachably connect the sleeve to the vacuum control valve and the patient module.

SUMMARY OF THE INVENTION

The present invention includes the provision of a hinged retaining collet with a snap lock closure. An end of the flexible sleeve is mounted over the tubular fitting, and the open retaining collet is then closed around the sleeve end and the fitting with closure being effected by the snap lock. The retaining collet and the fitting are provided respectively with interlocking slots and ribs which mechanically coact in resisting both rotation and axial movement of the collet with respect to the fitting on which it has been applied. The sleeve end need not be threaded through the split collet prior to being inserted over the tubular fitting, thus simplifying assembly procedures.

These and other objects and advantages of the present invention will become more apparent as the description proceeds with reference to the accompanying drawings.

DETAILED DESCRIPTION OF THE ILLUSTRATED EMBODIMENTS

Figure 1:
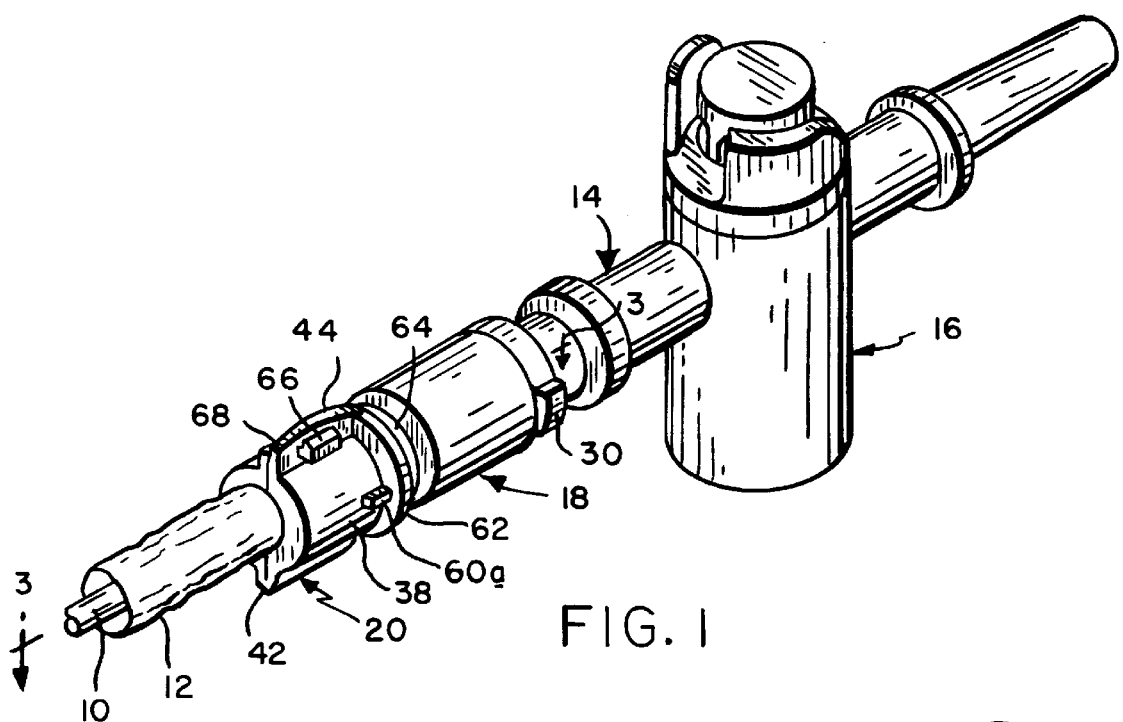
FIG. 1 is a perspective view showing the suction control valve of an aspirating catheter with a catheter enclosed within a flexible sleeve and connected to the valve by a fitting in accordance with the present invention.
Figure 2:
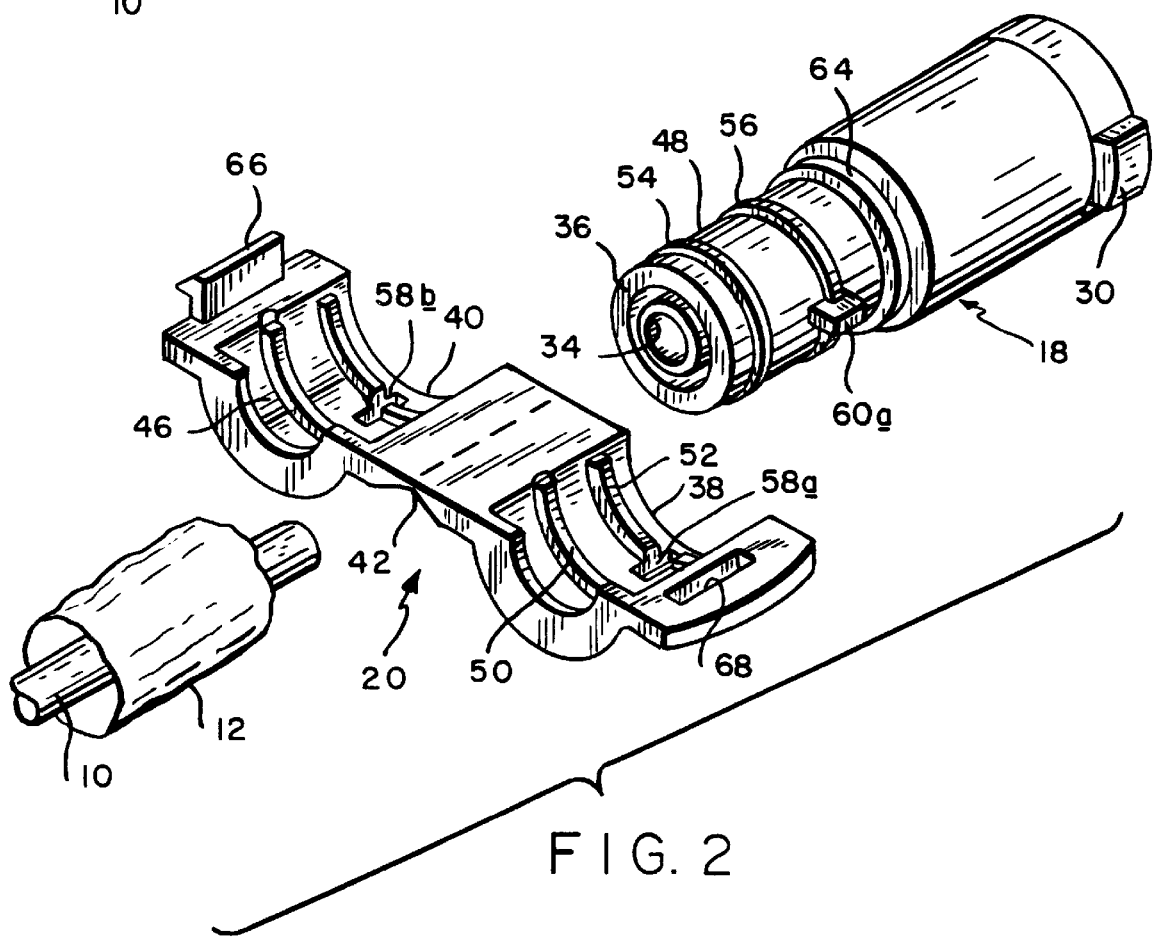
FIG. 2 is as an exploded perspective view of the fitting, one end of the protective sleeve and catheter, and the hinged collet prior to assembly.
Figure 3:
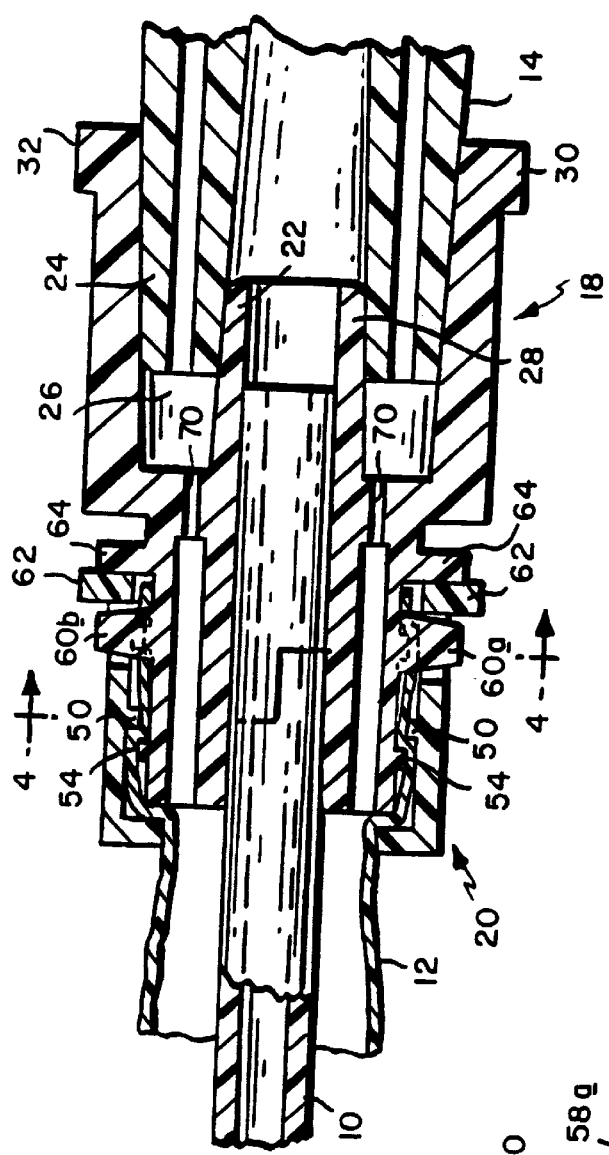
FIG. 3 is a sectional view on an enlarged scale taken along line 3—3 of FIG. 1.
Figure 4:
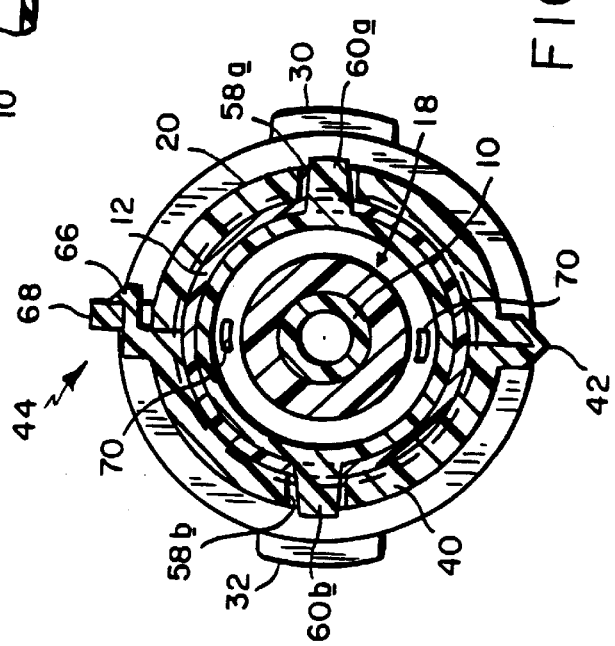
FIG. 4 is a sectional view taken along line 4—4 of FIG. 3.

With reference to the drawings, a catheter 10 is surrounded by a flexible sleeve 12, and both are connected to a tubular extension 14 of a suction control valve 16 by means of a tubular fitting 18 and a split collet 20 according to the present invention.

The suction control valve 16 is located at one end of an aspirating catheter. The opposite end of the aspirating catheter is detachably secured to a patient module (not shown) connected to a tracheostomy device installed in the trachea of a patient. Both the fitting 18 and the suction control valve 16 include two concentric male 22, 24 and female 26, 28 slidably engageable collars, respectively. Located at the distal end of the fitting 18 are two radial protrusions 30, 32 which can be grasped when engaging the fitting 18 with the tubular extension 14 of the control valve 16.

During assembly of the disclosed components, the catheter 10 is tightly received in an opening 34 at the proximate end of the fitting 36. The flexible sleeve 12 surrounding the catheter 10 is mounted over the outer surface of the proximal end of the tubular fitting 18. The sleeve 12 is secured in place by means of the split collet 20.

The collet 20 may be injection molded from any known polymeric material, e.g., polypropylene, and is comprised of two semi-circular segments 38, 40 connected at one side of each segment by an integrally formed flexible hinge 42. At the opposite side of each segment are complementary portions of a snap lock closure 44.

The collet 20 and the fitting 18 are provided with interengageable elements which prevent both rotational and axial movement of the collet with respect to the fitting. Located on the inside surface of the collet 46 and the outside surface of the fitting 48 are two sets of interengageable shoulders 50, 52 and 54, 56, respectively. When the collet 20 is fixed in place on the fitting 18, the shoulders 50, 52 on the collet abut the shoulders 54, 56 on the fitting to prevent any axial movement of the collet with respect to the fitting. Rotational fixing of the collet with respect to the fitting is achieved by the interengagement of ears 60a, 60b on the fitting which are received in apertures 58a, 58b in the two halves of the collet. Additional axial location of the collet on the fitting is provided by the circular outer collet rib 62 which abuts a circular shoulder 64 on the fitting.

The snap lock closure 44 preferably includes a tongue 66 and a slotted flange 68 through which the tongue is passed and mechanically engaged. The fitting 18 is preferably provided with internal venting passages 70 which accommodate a flow of air into and out of the sleeve 12 as it is collapsed and extended to accommodate insertion and retraction of the catheter 10 into and out of the patient.

Among the advantages associated with the present invention is the ease with which the collet 20 may be reliably secured to the proximal end of the fitting 18. A simple snap lock 14 is easily manipulated by the assembler, and the interengagement of the shoulders 54, 56 and ears 60a, 60b with respective shoulders 50, 52 and apertures 58a, 58b on the collet insures positive location coupled with a reliable fixation, both axially and rotationally. The sleeve 12 is securely and sealingly held between the exterior of the fitting and the interior of the collet.

In light of the foregoing, it will now be appreciated by those skilled in the art that the present invention provides a novel and significantly improved apparatus for securely attaching the protective sleeve of an aspirating catheter to a fitting.

The foregoing description has been set forth merely to illustrate the invention and is not intended to be limiting. Since modifications of the described embodiments incorporating the spirit and substance of the invention may occur to persons skilled in the art, the scope of the invention should be limited solely with reference to the appended claims and equivalents.

We claim:

1. Apparatus for shielding and detachably coupling one end of an aspirating catheter to a component of a patient ventilating and aspirating device, said apparatus comprising:
   a flexible sleeve for surrounding the catheter;
   a tubular fitting having one end adapted for detachable connection to the component and having a tubular extension at an opposite end for receiving an end of the catheter, said tubular extension inserted into one end of said sleeve; and
   a split collet having semicircular segments, said segments secured in an operative position tightly surrounding the end of said sleeve and the tubular extension inserted therein, said segments being coactively interengageable in said operative position in an axially and rotationally fixed relationship with respect to said tubular extension.

2. The apparatus of claim 1 further comprising:
   interengageable means on said tubular extension and at least one of said collet segments, said means on said extension and said collet segments interengage each other for resisting axial displacement of said collet in relation to said tubular extension.

3. The apparatus of claim 2, wherein said tubular extension has an exterior surface and said collet has an interior surface, and said interengageable means includes at least one circular shoulder on said exterior surface of said tubular extension and at least one complementary shoulder on said interior surface of said collet.

4. The apparatus of claim 2, further comprising a radial protrusion on said tubular extension, and wherein said interengageable means further includes an aperture in at least one of said collet segments adapted to receive said radial protrusion on said tubular extension.

5. The apparatus of claim 1, wherein said semicircular segments of said split collet each have a first side and a second side opposite the first side and are connected at adjacent first sides by an integral flexible hinge and have locking elements at opposite second sides.

6. The apparatus of claim 5, wherein said locking elements include a tongue on one of said collet segments and a slotted flange on the other of said collet segments.

7. The apparatus of claim 1, further comprising: interengageable means on an external surface of said tubular extension and on at least one of said collet segments, said means on said extension and said collet segments interengage each other for opposing rotation of said collet in relation to said tubular extension.

8. The apparatus of claim 7, wherein said interengageable means includes at least one integrally formed radial protrusion on said tubular extension and a complementary aperture in at least one of said collet segments.

9. The apparatus of claim 1, wherein said collet is injection molded of polypropylene.

10. Apparatus for shielding and detachably coupling an end of an aspirating catheter to a patient ventilating and aspirating device, said apparatus comprising:
    a flexible sleeve for surrounding the catheter;
    a tubular fitting having one end adapted for detachable connection to the patient ventilating and aspirating device and having a tubular extension at an opposite end for receiving an end of the catheter, said tubular extension inserted into one end of said sleeve; and
    a split collet having semicircular segments, said segments secured in an operative position tightly surrounding the end of said sleeve and the tubular extension inserted therein, said segments being coactively interengageable in said operative position in an axially fixed relationship with respect to said tubular extension and wherein said operatively positioned split collet is in a rotationally fixed relationship with respect to said tubular extension.

11. The apparatus of claim 10, wherein said semicircular segment of said split collet each have a first side and a second side opposite the first side and are connected at adjacent first sides by an integral flexible hinge and have locking elements at opposite second sides.

12. The apparatus of claim 11, wherein said locking elements include a tongue on one of said collet segments and a slotted flange on the other of said collet segments.

13. The apparatus of claim 10 further comprising:
    interengageable means on said tubular extension and at least one of said collet segments, said means on said extension and said collet segments interengage each other for resisting axial displacement of said collet in relation to said tubular extension.

14. The apparatus of claim 13, wherein said tubular extension have an exterior surface and said collet have an interior surface and said interengageable means includes at least one circular shoulder on said exterior surface of said tubular extension and at least one complementary shoulder on said interior surface of said collet.

15. The apparatus of claim 10, wherein said collet is injection molded of polypropylene.

16. Apparatus for shielding and detachably coupling an end of an aspirating catheter to a patient ventilating and aspirating device, said apparatus comprising:
    a flexible sleeve for surrounding the catheter;
    a tubular fitting having one end adapted for detachable connection to the patient ventilating and aspirating device and having a tubular extension with interengageable means on an external surface thereof at an opposite end for receiving an end of the catheter, said tubular extension inserted into one end of said sleeve; and
    a split collet having semicircular segments, and interengageable means on at least one of said collet segments said segments secured in an operative position tightly surrounding the end of said sleeve and the tubular extension inserted therein, said segments being coactively interengageable in said operative position in an axially fixed relationship with respect to said tubular extension and wherein, said means on said extension and said collet segments interengage each other for opposing rotation of said collet in relation to said tubular extension.

17. The apparatus of claim 16, wherein said interengageable means includes at least one integrally formed radial protrusion on said tubular extension and a complementary aperture in at least one of said collet segments.

18. Apparatus for shielding and detachably coupling an end of an aspirating catheter to a patient ventilating and aspirating device, said apparatus comprising:

a flexible sleeve for surrounding the catheter; a tubular fitting having one end adapted for detachable connection to the patient ventilating and aspirating device and having a tubular extension, with a radial protrusion thereon at an opposite end for receiving an end of the catheter, said tubular extension inserted into one end of said sleeve; and a split collet having semicircular segments, and an aperture in at least one of said collet segments said segments secured in an operative position tightly surrounding the end of said sleeve and the tubular extension inserted therein, said segments being coactively interengageable in said operative position in an axially fixed relationship with respect to said tubular extension, wherein said radial protrusion is received by said aperture.

* * * * *